United States Patent
Kashmer

[11] Patent Number: 5,807,351
[45] Date of Patent: Sep. 15, 1998

[54] PROTECTION DEVICE FOR SHARP OBJECTS

[75] Inventor: James S. Kashmer, Andover, N.J.

[73] Assignee: SafeGard Medical Products, Inc., Woburn, Mass.

[21] Appl. No.: 664,352

[22] Filed: Jun. 17, 1996

[51] Int. Cl.$^6$ .................................................. A61M 5/00
[52] U.S. Cl. ................................ 604/263; 604/192
[58] Field of Search .................... 604/263, 192, 604/187, 110

[56] References Cited

U.S. PATENT DOCUMENTS

| | | |
|---|---|---|
| 4,982,842 | 1/1991 | Hollister . |
| 5,151,089 | 9/1992 | Kirk, III et al. .................. 604/192 |
| 5,188,611 | 2/1993 | Orgain . |
| 5,312,368 | 5/1994 | Haynes . |
| 5,486,163 | 1/1996 | Haynes . |
| 5,490,841 | 2/1996 | Landis .................... 604/263 X |
| 5,509,907 | 4/1996 | Bevilacqua .................. 604/263 |

*Primary Examiner*—John D. Yasko
*Attorney, Agent, or Firm*—Choate, Hall & Stewart

[57] ABSTRACT

A shielding apparatus for preventing accidental contact with a sharp object such as a needle. The apparatus comprises a hinged shield, a barrel and a locking mechanism. The apparatus is attached to an existing needle via a barrel or may be manufactured into the base of the syringe needle. Connected to the barrel is a hinge, a shield and a locking mechanism. The shield may pivot, via the hinge, in a direction away from needle so as to expose the needle for use. Upon completion of the use, the shield is pivoted so as to cover the needle, the shield being either permanently or temporarily locked in place via the locking mechanism, thereby preventing accidental contact.

27 Claims, 2 Drawing Sheets

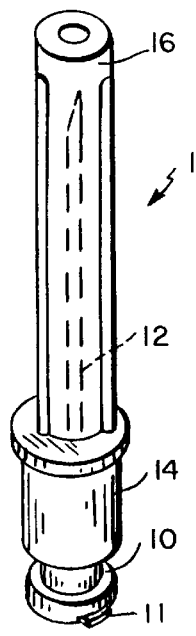
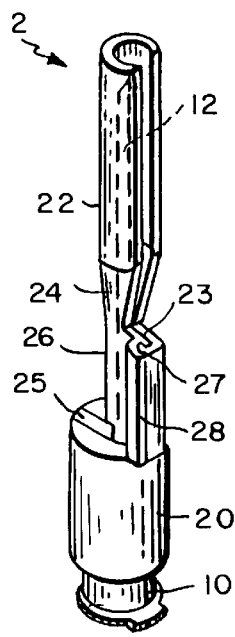
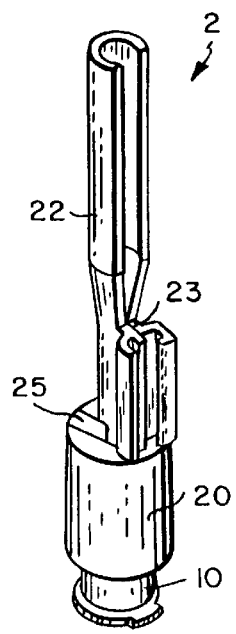
FIG. 1 PRIOR ART    FIG. 2(a)    FIG. 2(b)
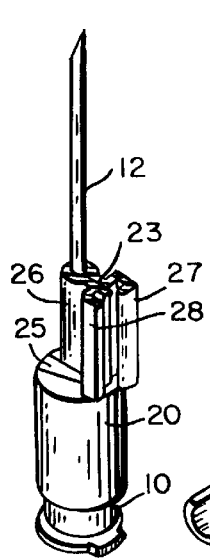
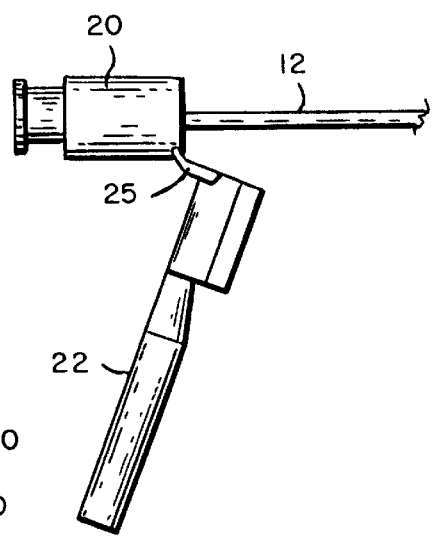
FIG. 2(c)    FIG. 3(a)    FIG. 3(b)

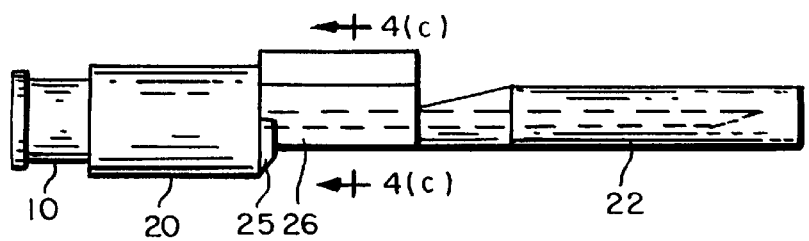
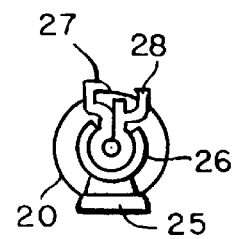
FIG. 4(a)  FIG. 4(b)
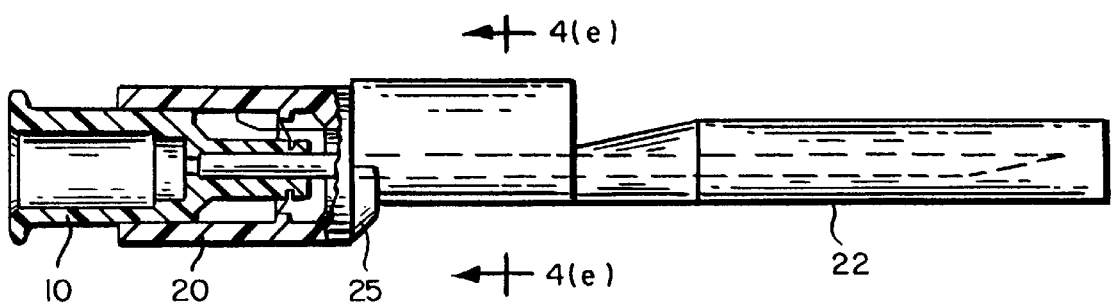
FIG. 4(d)
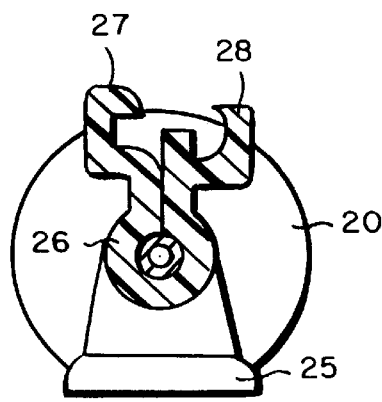
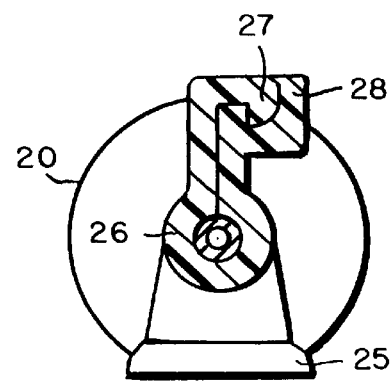
FIG. 4(c)  FIG. 4(e)

PROTECTION DEVICE FOR SHARP OBJECTS

BACKGROUND OF THE INVENTION

The present invention relates generally to a protective device to prevent accidental contact with the sharp surface of an object and more particularly to a protective device having a locking mechanism to prevent reuse of a needle.

While the accidental needle sticks have always plagued healthcare practitioners, the advent of AIDS and various other potentially lethal blood borne pathogens has increased the consequences of such needle sticks. Various attempts have been made to minimize such risks. For instance, devices have been introduced to shield the healthcare practitioner from making contact with a potentially contaminated needle, but have met with limited effectiveness.

A needle protection device (or shield) must meet certain criteria to be effective. First, it must provide protection to the healthcare practitioner—in other words provide an effective barrier to prevent accidental contact with the needle. Second, it must be simple to use so that the healthcare practitioner can effectively perform his or her job while at the same time avail themselves of the protection afforded by the protection device. Third, it must be cost effective so that hospitals will not incur undue costs. Fourth, it must provide protection on a time basis to shield all healthcare workers from the device.

In addition to the criteria listed, a protective device should also prevent exposure of the needle once disposed, be intuitive to use and accommodate a variety of needle sizes.

Past designs for needle protection devices included various forms of pivoting shrouds or shields that surround the needle. These designs can be divided into two broad categories based upon the locking mechanism. The first category utilized a reversible locking mechanism. This design allows the healthcare practitioner to repeatedly use the shrouding mechanism. Thus, a healthcare practitioner can engage the lock after filling the hypodermic syringe and remove the shroud just prior to injection. But this type of locking mechanism does not allow for permanent locking of the shroud about the needle, preventing reuse. The second category of needle protection devices utilizes a single use locking mechanism. This design prevents the healthcare practitioner from repeatedly using the shrouding mechanism. So a healthcare practitioner can engage the lock only after final use of the needle, just prior to disposal.

Neither of the two broad categories provide for both a temporary locking mechanism and a permanent locking mechanism. Thus, neither of the two designs allow for temporary locking of the shroud about the needle for intermediate protection and permanent locking of the shroud about the needle for final protection and disposal.

SUMMARY OF THE INVENTION

Accordingly, it is an object of the present invention to provide a needle shield that prevents accidental needle contact by the healthcare provider.

It is a further object of the invention to provide a needle shield that does not interfere with the normal operation of the syringe.

It is an additional object of the invention to provide a needle shield that pivots away from the needle to allow use application of the needle.

It is another object of the invention to provide a needle shield that may be used with pre-existing needles and not require redesign of the pre-existing needle.

It is another object of the invention to provide a needle shield with a temporary locking mechanism to prevent exposure of the needle.

It is another object of the invention to provide a needle shield with a permanent locking mechanism to prevent reuse.

It is an additional object of the invention to provide a needle shield having a locking mechanism that engages under the control of the healthcare practitioner.

It is a further object of the invention to provide a needle shield that is cost effective to produce.

Other objects will be obvious and will appear hereinafter. The invention comprises an article of manufacture as exemplified in the following summary and detailed description.

The protection device of the present invention is an assembly which is integrally molded with the a needle assembly or separately fabricated and later mated to a needle via the needle hub. The protection device includes a collar which is either compression fitted to or integrally molded with the needle hub. Attached to the hub is a hinge that ultimately allows the shield portion of the assembly to pivot away from the needle. The hinge is mated to channel portion, which is itself mated to a transition portion connected to the shield. The channel portion is sized so as to frictionally engage the needle shaft, thereby creating a temporary locking mechanism to hold the shield next to the needle. Disposed upon the channel portion is a permanent locking mechanism. The permanent locking mechanism locks the shield in the protective position, permanently shielding the needle.

The present invention further includes variations on this design. The temporary locking mechanism may be placed in the shield assembly or disposed in the transition piece. In addition, the permanent locking mechanism may be placed in any location, including the shield, and may further comprise a one-way lock. The hinge may be formed as a single or multiple piece design.

The above mentioned objectives of the present invention will become more apparent and the invention itself better understood with reference to the following description of the embodiments of the present invention in conjunction with the accompanying drawings.

BRIEF DESCRIPTION OF THE DRAWINGS

The foregoing discussion will be understood more readily from the following detailed description of the invention, when taken in conjunction with the accompanying drawings, in which:

FIG. 1 is a perspective view of a prior art shield;

FIG. 2(a) is a front perspective view of an embodiment of the invention illustrating the shield in the closed and locked position;

FIG. 2(b) is a front perspective view of an embodiment of the invention illustrating the shield in the closed and unlocked position;

FIG. 2(c) is a front perspective view of an embodiment of the invention illustrating the shield in the closed and unlocked position;

FIG. 3(a) is a side perspective view of an embodiment of the invention illustrating the shield in the open and unlocked position with the needle cover pivoted away from the needle;

FIG. 3(b) is a side view of an embodiment of the invention illustrating the shield in the open and unlocked position with the needle cover pivoted away from the needle;

FIG. 4(a) is a side view of an embodiment of the invention illustrating the shield in the closed and unlocked position;

FIG. 4(b) is an end view of an embodiment of the invention illustrating the shield in the closed and unlocked position;

FIG. 4(c) is an end view through the section A—A of FIG. 4(a) of an embodiment of the invention illustrating the shield in the closed and unlocked position;

FIG. 4(d) is a side view of an embodiment of the invention illustrating the shield in the closed and locked position; and FIG. 4(e) is an end view through the section B—B of FIG. 4(d) of an embodiment of the invention illustrating the shield in the closed and locked position.

DETAILED DESCRIPTION OF THE PREFERRED EMBODIMENT

Referring to FIG. 1, a prior art needle conventional needle shield assembly mounted on a needle is illustrated. The shield assembly 1 comprises a base or collar 14 attached to a shield 16. Shield 16 is hollow cylinder disposed around the needle shaft 12. The base or collar 14 is dimensioned so as to friction fit over hub 10 in manner so as to not interfere with luer tabs 11. Removal of the shield assembly entails uncoupling base or collar 14 from hub 10 and sliding the shield 16 up and over needle 12. Conversely, replacement of the shield assembly 1 entails sliding the needle 12 into cylinder 16 and friction fitting base 14 to hub 10.

FIGS. 2(a), 2(b) and 2(c) illustrates an embodiment of the present invention as utilized in conjunction with a pre-existing needle. The shield assembly 2 of the present invention is comprised of a barrel 20 that permanently holds the assembly 2 to the needle hub 10. The barrel 20 and the hub 10 may be fictionally fit to one another or molded into a single unit. Above the barrel 20 is the locking mechanism which connects to the barrel 20 via hinge 25. The locking mechanism includes temporary lock formed by a channel portion 26 sized to frictional fit the needle 12. A slit 23 in channel portion 26 allows passage of the needle 12 when channel portion 26 is pivoted about the hinge 25. A permanent lock, disposed on opposite sides of slit 23, is formed by a pivoting latch 27 and a catch 28.

Above the channel portion is a transition piece 24 which allows for a transition between the channel portion 26 and shield 22. Shield 22 is sized and shaped to enclose the needle 12 so as to prevent accidental contact. As illustrated, the shield 22 is a cylindrical portion extending beyond the tip of the needle 12 and substantially surrounding the needle 12.

FIG. 2(a) illustrates the shield assembly 2 in the closed and locked position with the shield 22 enclosing the needle 12 and the locking mechanism 27 and 28 locked. As illustrated, the needle 12 is disposed in the channel 26 and enclosed by the latch 27 engaged to the catch 28. FIG. 2(b) illustrates the shield assembly 2 in the closed and unlocked position with the locking mechanism now in the unlocked position. FIG. 2(c) is a cutaway with the shield 22 removed, illustrating the shield assembly 2 in the closed and unlocked position.

The shield assembly 2 is designed to pivot away from the needle 12 via a hinge 25. FIGS. 3(a) illustrates the pivoting action of the shield assembly into the open and unlocked position. In this position, the needle 12 is exposed for use. FIG. 3(b) is a side view of the assembly in the open position. Again, in this position the needle is unobstructed.

In order to cover the needle, the shield 22 is pivoted into the closed position via hinge 25. FIGS. 4(a) is a side view illustrating the assembly in the closed and closed position. In this position, the needle 12 is temporarily secured in channel portion 26. Friction between the needle 12 and the channel portion 26 prevents the shield 22 from accidently pivoting into the open position. The shield 22 is not permanently locked, but rather temporarily locked in this configuration. By overcoming the friction between the needle 12 and the channel portion 26, the healthcare provider can once again pivot the assembly into the open position, exposing the needle. Thus, the present invention allows the shield assembly to cover the needle multiple times, such as prior to filling, after filling but prior to injection, and after injection but prior to disposal.

Once the healthcare provider has determined that the procedure is complete and that the needle should be disposed, the shield assembly is permanently locked in the closed position. With reference to FIGS. 2(b), 4(a), and 4(b) the needle 12 is first captured into the channel assembly 26. Next, the locking mechanism is engaged by swinging the pivoting latch 27 to the catch 28 which form the permanent lock. FIGS. 2(a), 4(d) and 4(e) illustrate how latch 27 engages and locks into catch 28. It is preferred that the lock formed by the latch 27 and the catch 28 be of a one-way design so that, once engaged, the latch 27 cannot be separated from the catch 28. Thus, the preferred design for the lock assembly prevents unlocking once the permanent lock is engaged. Once the shield assembly is in the locked closed position, the needle may be disposed.

Variations on the design are envisioned. For instance, in the preferred design, the hinge 25 is formed as a single piece "living hinge," but a two piece hinge is also contemplated. The preferred design for the temporary lock is the channel 26 which fictionally engages the needle 12, but alternative designs utilizing temporary locks disposed in shield 22 are also contemplated. In addition, the permanent lock in the preferred embodiment utilizes a latch 27 and a catch 28 disposed on opposite sides of the channel 26, but may also be composed of various permanent locks disposed in the shield 22 and may also utilize various shapes for the latch 27 and the catch 28.

The shield assembly of the preferred embodiment can be constructed from a thermoplastic material via an injection molding process. The shroud may be integrally molded with the needle hub or may be molded separately and press fit to needle hub. The preferred material would be of the polyolefin family, which includes polyethylene and polypropylene, because of the embodiments "living hinge." One of ordinary skill in the art would understand to select the final choice of material based upon such factors such as construction method, material compatibility, cost, etc.

It should be understood that other embodiments could be created with variations in shape and size. Although the present invention has been described in detail with reference only to present preferred embodiments, it will be appreciated by one of ordinary skill in the art that various modifications can be made without departing from the invention. Accordingly, the invention is limited only by the following claims.

What is claimed is:

1. An apparatus to cover a needle comprising:
    a collar adapted to engage a first portion of the needle;
    a shield adapted to cover at least a second portion of the needle, said shield in communication with said collar via a hinge, said hinge allowing said shield to pivot away from said second needle portion; and
    a locking mechanism adapted to provide a temporary locking state and a permanent locking state, said locking mechanism having a channel portion adapted to surround a third portion of said needle in said temporary locking state when said shield is pivoted so as to cover said second needle portion, said locking mechanism further adapted to controllably engage said needle within said shield in said permanent locking state, whereby said shield reversibly covers said needle when in said temporary locking state and irreversibly covers said needle when in said permanent locking state.

2. The apparatus of claim 1 wherein said collar is further adapted to slide over said needle.

3. The apparatus of claim 1 wherein said needle further has an outer needle diameter, and said channel portion having an internal channel dimension approximately equal to said outer needle diameter so as to frictionally contact said needle thereby providing said temporary locking state.

4. The apparatus of claim 1 wherein said locking mechanism further comprises a one-way lock adapted to enclose said needle thereby providing said permanent locking state.

5. The apparatus of claim 4 wherein said one-way lock further comprises a latch and a catch for said latch.

6. The apparatus of claim 5 wherein said latch and said catch are disposed on said channel.

7. The apparatus of claim 4 wherein said one-way lock is integral to said shield.

8. The apparatus of claim 4 wherein said channel is disposed between said hinge and said shield.

9. The apparatus of claim 6 where said locking mechanism is disposed between said hinge and said shield.

10. The apparatus of claim 1 wherein said shield surrounds at least half a circumference of a circle orthoganal to an axial direction of said needle.

11. The apparatus of claim 1 wherein said shield has a substantially cylindrical cross sectional shape.

12. The apparatus of claim 1 wherein said shield has a substantially rectangular cross sectional shape.

13. The apparatus of claim 1 wherein said locking mechanism is internal to said shield.

14. The apparatus of claim 1 wherein said collar, said shield, said hinge and said locking mechanism are formed of as a single unit.

15. An apparatus to cover a needle comprising, collar means adapted to engage a first portion of the needle;

shield means adapted to cover at least a second portion of the needle, said shield in communication with said collar means via hinge means, said hinge means allowing said shield means to pivot away from said second needle portion; and locking means adapted to provide a temporary locking state and a permanent locking state, said locking means adapted to engage said needle in said temporary locking state when said shield means is pivoted so as to cover said second needle portion, said locking means further adapted to controllably engage said needle within said shield means in said permanent locking state, whereby said shield means reversibly covers said needle when in said temporary locking state and irreversibly covers said needle when in said permanent locking state.

16. The apparatus of claim 15 wherein said collar means is further adapted to slide over said needle.

17. The apparatus of claim 15 wherein said needle further has an outer needle diameter, and said locking means having a channel portion having an internal channel dimension approximately equal to said outer needle diameter so as to fictionally contact said needle thereby providing said temporary locking state.

18. The apparatus of claim 15 wherein said locking means further comprises a irreversible locking means adapted to enclose said needle thereby providing said permanent locking state.

19. The apparatus of claim 16 wherein said irreversible locking means further comprises a latch and a catch for said latch.

20. The apparatus of claim 16 wherein said irreversible locking means is internal to said shield means.

21. The apparatus of claim 16 wherein said channel is disposed between said hinge and said shield.

22. The apparatus of claim 16 where said locking means is disposed between said hinge means and said shield means.

23. The apparatus of claim 15 wherein said shield means surrounds at least half a circumference of a circle orthoganal to an axial direction of said needle.

24. The apparatus of claim 15 wherein said shield means has a substantially cylindrical cross sectional shape.

25. The apparatus of claim 15 wherein said shield means has a substantially rectangular cross sectional shape.

26. The apparatus of claim 15 wherein said locking means is internal to said shield means.

27. The apparatus of claim 15 wherein said collar means, said shield means, said hinge means and said locking means are formed of as a single unit.

\* \* \* \* \*